United States Patent
Nutman et al.

(10) Patent No.: US 9,068,993 B2
(45) Date of Patent: Jun. 30, 2015

(54) DIAGNOSTIC ASSAYS AND METHODS OF USE FOR DETECTION OF FILARIAL INFECTION

(75) Inventors: Thomas B. Nutman, Chevy Chase, MD (US); Doran Fink, Silver Spring, MD (US); Joseph Kubofcik, Catonsville, MD (US); Peter D. Burbelo, Washington, DC (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 40 days.

(21) Appl. No.: 13/882,850

(22) PCT Filed: Oct. 31, 2011

(86) PCT No.: PCT/US2011/058561
§ 371 (c)(1),
(2), (4) Date: Jun. 13, 2013

(87) PCT Pub. No.: WO2012/061281
PCT Pub. Date: May 10, 2012

(65) Prior Publication Data
US 2013/0273111 A1 Oct. 17, 2013

Related U.S. Application Data

(60) Provisional application No. 61/410,239, filed on Nov. 4, 2010.

(51) Int. Cl.
*G01N 33/53* (2006.01)
*G01N 33/567* (2006.01)
*G01N 33/569* (2006.01)
*G01N 33/68* (2006.01)
*C07K 14/435* (2006.01)

(52) U.S. Cl.
CPC ........ *G01N 33/6893* (2013.01); *C07K 14/4354* (2013.01); *G01N 33/569* (2013.01); *G01N 2333/4353* (2013.01)

(58) Field of Classification Search
CPC .................................................. G01N 33/6893
See application file for complete search history.

(56) References Cited

U.S. PATENT DOCUMENTS

| 5,225,539 A | 7/1993 | Winter |
| 5,449,752 A | 9/1995 | Fujii et al. |
| 5,545,806 A | 8/1996 | Lonberg et al. |
| 5,569,825 A | 10/1996 | Lonberg et al. |
| 5,585,089 A | 12/1996 | Queen et al. |
| 5,639,641 A | 6/1997 | Pedersen et al. |
| 5,639,761 A | 6/1997 | Francois et al. |
| 5,693,761 A | 12/1997 | Queen et al. |
| 5,714,352 A | 2/1998 | Jakobovitz |
| 6,265,150 B1 | 7/2001 | Terstappen et al. |
| 2002/0197266 A1 | 12/2002 | Debinski |
| 2007/0259336 A1 | 11/2007 | Burbelo et al. |

FOREIGN PATENT DOCUMENTS

| EP | 0 239 400 A2 | 9/1987 |
| GB | 2 188 638 A | 10/1987 |

OTHER PUBLICATIONS

Steel, C. et al., "Rapid wuchereria bancrofti-specific antigen Wb123-based IgG4 immunoassays as tools for surveillance following mass drug administration programs on lymphatic filariasis," *Clinical and Vaccine Immunology*, 20(8), 1155-1161 (2013).
Baskar et al., "Development and evaluation of a rapid flow-through immuno filtration test using recmobinant filarial antigen for diagnosis of brugian and bancroftian filariasis," *Microbiol Immunol.*, 48(7), 519-25 (2004).
Burbelo et al., "A simplified immunoprecipitation method for quantitatively measuring antibody responses in clinical sera samples by using mammalian-produced Renilla luciferase-antigen fusion proteins," *BMC Biotechnol.*, 5, 22 (Aug. 18, 2005).
Burbelo et al., "High definition profiling of autoantibodies to glutamic acid decarboxylases GAD65/GAD67 in stiff-person syndrome," *Biochem Biophys Res Commun.*, 366(1), 1-7 (2008).
Burbelo et al., "Rapid, novel, specific, high-throughput assay for diagnosis of Loa loa infection," *J Clin Microbiol.*, 46(7), 2298-304 (Jul. 2008).
EBI Database Accession No. EM__INV: HQ438580 (Jun. 3, 2011).
Guo et al., "dCAS: a desktop application for cDNA sequence annotation," *Bioinformatics*, 25(9), 1195-6 (May 1, 2009).
Haskard et al., "The production of human monoclonal autoantibodies from patients with rheumatoid arthritis by the EBV-hybridoma technique," *J Immunol Methods*, 74(2), 361-7 (Nov. 30, 1984).
Hudecz, "Synthesis of peptide bioconjugates," *Methods Mol Biol.*, 298, 209-23 (2005).
Huse et al., "Generation of a large combinatorial library of the immunoglobulin repertoire in phage lambda," *Science*, 246(4935), 1275-81 (Dec. 8, 1989).
International Preliminary Report on Patentability, Appln. No. PCT/US2011/058561, dated May 16, 2013.
International Search Report, Appln. No. PCT/US2011/058561, dated Feb. 14, 2012.
Kirin et al., "Amino acid and peptide bioconjugates of copper(II) and zinc(II) complexes with a modified N,N-bis(2-picolyl)amine ligand," *Inorg Chem*, 44(15), 5405-15 (Jul. 25, 2005).
Kohler et al., "Derivation of specific antibody-producing tissue culture and tumor lines by cell fusion," *Eur J Immunol.*, 6(7), 511-9 (Jul. 1976).

(Continued)

*Primary Examiner* — Albert Navarro
(74) *Attorney, Agent, or Firm* — Leydig, Voit & Mayer

(57) ABSTRACT

The polynucleotide encoding the antigen Wb123 from the filarial nematode *Wuchereria bancrofti*, the major causative organism of lymphatic filariasis is provided, along with the polypeptide encoded by the polynucleotide. Methods for making the WM23 antigen, recombinant vectors encoding the Wb123 polynucleotide, and methods of detection of the Wb123 antigen through luciferase immunoprecipitation, ELISA and other detection systems are also provided.

10 Claims, 8 Drawing Sheets

(56) References Cited

OTHER PUBLICATIONS

Kubofcik et al., "Identification of Wb123 as an early and specific marker of *Wuchereria bancrofti* infection," *PLoS Negl Trop Dis.*, 6(12), e1930 (2012).

Lal et al., "Enhanced diagnostic specificity in human filariasis by IgG4 antibody assessment," *J Infect Dis.*, 158(5), 1034-7 (Nov. 1988).

Lammie et al., "Recombinant antigen-based antibody assays for the diagnosis and surveillance of lymphatic filariasis—a multicenter trial," *Filaria J.*, 3(1), 9 (Sep. 3, 2004).

Lipner et al., "Field applicability of a rapid-format anti-Ov-16 antibody test for the assessment of onchocerciasis control measures in regions of endemicity," *J Infect Dis*, 194(2), 216-21 (Jul. 15, 2008).

Lobos et al., "An immunogenic *Onchocerca volvulus* antigen: a specific and early marker of infection," *Science*, 251 (5001), 1603-5 (Mar. 29, 1991).

Miranda et al., "Perfil protéico e reconhecimento antigênico de extratos de larvas infectantes (L3) de *Wuchereria bancrofti*—Proteic profile and antigenic recognition of extracts from *Wuchereria bancrofti* L3 infective larvae," *Rev Soc Bras Med Trop*, 38(1), 27-32 (2005) (English Abstract).

Pederson et al., "Comparison of surface accessible residues in human and murine immunogloubulin Fv domains. Implication for humanization of murine antibodies," *J Mol Biol.*, 235(3), 959-73 (Jan. 21, 1994).

Roder et al., "The EBV-hybridoma technique," *Methods Enzymol.*, 121, 140-67 (1986).

Saverimuttu et al., "A preliminary analysis of *Wuchereria bancrofti* microfilarial antigens for potential use in diagnosis," *Southeast Asian J Trop Med Public Health*, 31(2), 252-8 (Jun. 2000).

Steel et al., "Antibody to tie filarial antigen Wb123 reflects reduced transmission and decreased exposure in children born following single mass drug administration (MDA)," *PLoS Negl Trop Dis.*, 6(12), e1940 (2012).

Vasu et al., "A 43-kDa circulating filarial antigen fraction of *Wuchereria bancrofti* in immunoprophylaxis against *Brugia malayi* in jirds," *Parasitol Int.*, 48(4), 281-8 (Feb. 2000).

Weil et al., "A multicenter evaluation of a new antibody test kit for lymphatic filariasis employing recombinant *Brugia malayi* antigen Bm-14," *Acta Trop.* 120 Suppl 1, S19-22 (Apr. 27, 2010).

FIGURE 1

ATCCTGGGCCAGATCAGCCTGACCGACCGGGCCCAGCTGGACTTCGCCGTGAAC
CTGCTGCAGAACGTGGCCGAGAGCGACCGGAGCAGCATCCTGAGCCCCTTCAGC
GTGAGCACCAGCCTGTTCATCGCCTACCTGGCAGCAGACGGAGAGACCAAGCAG
CAGCTGCAGAACGCACTGGGCAAGACCGCAAGCACCAGCCAGTTCAGAATCCAC
TTCGCCAAGCAGCTGGCCTACCTGGCCCGGGCCGAGAGCCGGAACTACACCCTG
AACGTGGCCAACCGGTTCTACGTGCGGGAGGAGTTCAGCACCAAGGAGAGCTTC
CAGCGGGTGCTGAGCTTCTACTACAACGAGATCCTGTACAAGTTCAACTTCGAGC
AGCGGAACGAGCTGGTGCAGGAGATCAACGACTGGGTGAGCAACGAGACCAAC
AACAAGGTGACCAAGATGATCACCGAGAACAGCATCACCGAGGACACCCGGATG
CTGCTGATGAACGCCATCCACTTCAAGGGCACCTGGACCACCCAGTTCATCGACT
TCGTGACCAAGCAGAAGCAGTTCCACATCAGCGAGAACGAGGTGAAGCTGGTGC
CCATGATGGCCAAGAGCGACACCGTGCCCTACTACGAGGACGACGTGGTGAAAG
TGATCAAGCTGCCCTACACCGGAGGAGAGGTGGAGATGGTGGTCATCCTGCCAA
AGCGGCGGTTCGGACTGAGCGACGTGCTGAAGAACCTGAGCGGCGAGAAGCTGC
TGAAGTACGTGAACGAGGCCAAGAACCGGACCGTGAGCATCCGGATGCCCCGGT
TCCAGGTGGAGGAGAAGCGGAACCTGAACAACGCCCTGCAGGCCATCGGCATCA
CCGACGCCTTCAGCGGCAAGGCCGACTTCGGCGAGCTGCTGAACAACAGCATCC
CCATCAGCATCGGCAAGATCATCCACGCCGGCTTCATCGAGGTGAACGAGAAGG
GCACCGAGAGCGCCGCAGCCACCCTGATCGAGCTGGAGGACAGGATGGCAAGCA
GCCGGAACTTCAACGCCGACGAGCCCTTCCTGTTCGCCATCGTGAAGGACCTGAA
GACCGTGCTGTTCATCGGCCAGTTCGTGAAGTGA (SEQ ID NO: 1)

FIGURE 5A

| | Plasmid Name | Name | Forward Primer Name | Forward Sequence | Rev Primer Name | Reverse Sequence |
|---|---|---|---|---|---|---|
| 1 | Bm134 | BmHypothetical | BM134-5p-Bam | GAGGGATCCATGCCACTGAT GTACCAGTAC (SEQ ID NO: 2) | BM134-3p-Xho | GAGCTCGAGTCAGCAGAAGGTCTTGGCGAT (SEQ ID NO: 3) |
| 2 | Bm222 | BmHypothetical | BM222-5p-Bam | GAGGGATCCATGTTCCTGCA GAAGAAGGAC (SEQ ID NO: 4) | BM222-3p-Xho | GAGCTCGAGTCACAGCAGCCGCTGCTGCCA (SEQ ID NO: 5) |
| 3 | Bm24 | BmVAH | BM24-5p-Bam | GAGGGATCCATGACCAGCCG GCACCGGCAC (SEQ ID NO: 6) | BM24-3p-Xho | GAGCTCGAGTCAGTCGAAGCACAGGTTCAG (SEQ ID NO: 7) |
| 4 | Bm373 | BmES62 | BM373-5p-Bam | GAGGGATCCAGCCAGAACTA CGTGCTGGAG (SEQ ID NO: 8) | BM373-3p-Xho | GAGCTCGAGTCACTTGATCAGCACGCCGAT (SEQ ID NO: 9) |
| 5 | Bm419 | Bmpde-2 | BM419-5p-Bam | GAGGGATCCATGTACAACGA CGAGAGCGTG (SEQ ID NO: 10) | M419-3p-Xho | GAGCTCGAGTCAGCCCAGGTCCCGCTCCG (SEQ ID NO: 11) |
| 6 | Bm499 | WbHypothetical | BM499-5p-Bam | GAGGGATCCATGAGCACCCT GGAGAACGCC (SEQ ID NO: 12) | BM499-3p-Xho | GAGCTCGAGTCAGCACAGGTTGATGGTGCA (SEQ ID NO: 13) |
| 7 | Bm698 | Bm-wnk- | 1BM698-5p-Bam | GAGGGATCCATGCTGAAGGG CCTGCAGCAC (SEQ ID NO: 14) | M698-3p-Xho | GAGCTCGAGTCAGCTCTCGCCGGTCACCAT (SEQ ID NO: 15) |
| 8 | Bm827 | BmHypothetical | BM827-5p-Bam | GAGGGATCCATGACCCTGGC CATCGGCGCC (SEQ ID NO: 16) | BM827-3p-Xho | GAGCTCGAGTCAGAAAGGGCTGCCGCTCGTT (SEQ ID NO: 17) |
| 9 | Bm97 | BmEpicuticulin | BM97-5p-Bam | GAGGGATCCCTGCACAAGCA CAACGCCCAC (SEQ ID NO: 18) | BM97-3p-Xho | GAGCTCGAGTCACTGCCAGTTCTGCAGCTG (SEQ ID NO: 19) |

FIGURE 5B

| 10 | Wb123 | WbSemin | WB123-5p-Bam | GAGGGATCCATCCTGGGCCAGATCACCCTG (SEQ ID NO: 20) | W13123-3n-Xhr | GAGCTCGAGTCACTTCACGAACTGGCCGAT (SEQ ID NO: 21) |
|---|---|---|---|---|---|---|
| 11 | Wb126 | WbHypothetical | WB126-5p-Bam | GAGGGATCCCGGAGCCCCGGCATCGAGGGC (SEQ ID NO: 22) | WB126-3p-Xho | GAGCTCGAGTCAGTAGCCGGGGGCGGTCCG (SEQ ID NO: 23) |
| 12 | Wb132 | WbEndochitinase | WB132-5p-Bam | GAGGGATCCATGAAAGAGCGCCTTCGTCGAG (SEQ ID NO: 24) | B132-3p-Xho | GAGCTCGAGTCAGGTGGGCAGCTCGGGGTT (SEQ ID NO: 25) |
| 13 | Wb153 | WbHypothetical | WB153-5p-Bam | GAGGGATCCATGCCCTTCCTGTTCTGCGAC (SEQ ID NO: 26) | WB153-3p-Xho | GAGCTCGAGTCACTGCTTGTAGGGCAGCCT (SEQ ID NO: 27) |
| 14 | Wb261 | WbHypothetical | WB261-5p-Bam | GAGGGATCCATGTGCACCGACGCCAACAGC (SEQ ID NO: 28) | B261-3p-Xho | GAGCTCGAGTCAGTTGTTCTTGTTCACGAT (SEQ ID NO: 29) |
| 15 | Wb267 | WbHypothetical | WB267-5p-Bam | GAGGGATCCATGAACAGCCAGACCGAGACC (SEQ ID NO: 30) | WB267-3p-Xho | GAGCTCGAGTCACTCGGTCAGGGTGATGAA (SEQ ID NO: 31) |
| 16 | Wb289 | WbHypothetical | WB289-5p-Bam | GAGGGATCCTTCGAGACCTGCGTGGACAAG (SEQ ID NO: 32) | WB289-3p-Xho | GAGCTCGAGTCAGTGCACCTGCTCGTTCAT (SEQ ID NO: 33) |
| 17 | Wb352 | WbHypothetical | WB352-5p-Bam | GAGGGATCCATGGTGACCATCGTGAGCAAG (SEQ ID NO: 34) | WB352-3p-Xho | GAGCTCGAGTCAGTTGCCGATGCCGTCCTC (SEQ ID NO: 35) |
| 18 | Wb443 | WbHypothetical | WB443-5p-Bam | GAGGGATCCATGCTGGCCGAGATCAGCAGC (SEQ ID NO: 36) | WB443-3p-Xho | GAGCTCGAGTCACAGCTTGGGCCGGCTCAT (SEQ ID NO: 37) |
| 19 | Wb610 | Wbpat-6 | WB610-5p-Bam | GAGGGATCCATGCCCTTCCTGTTCTGCGAC (SEQ ID NO: 38) | WB610-3p-Xho | GAGCTCGAGTCACTGCTTGTAGGGCAGCCT (SEQ ID NO: 39) |

FIGURE 6A

| | Plasmid Name | Name | Fwd Primer Name | Sequence Specific Forward Primer | Rev Primer Name | Sequence Specific Reverse Primer |
|---|---|---|---|---|---|---|
| 1 | Bm134 | BmHypothetical | BM134-5p | ATGCCACTGATGTACCAGTAC (SEQ ID NO: 40) | BM134-3p | TCAGCAGAAGGTCTTGGCGAT (SEQ ID NO: 41) |
| 2 | Bm222 | BmHypothetical | BM222-5p | ATGTTCCTGCAGAAGAAGGAC (SEQ ID NO: 42) | BM222-3p | TCACAGCAGCCGCTGCTGCCA (SEQ ID NO: 43) |
| 3 | Bm24 | BmVAH | BM24-5p | ATGACCAGCCGGCACCGGCAC (SEQ ID NO: 44) | BM24-3p | TCAGTCGAAGCACAGGTTCAG (SEQ ID NO: 45) |
| 4 | Bm373 | BmES62 | BM373-5p | AGCCAGAACTACGTGCTGGAG (SEQ ID NO: 46) | BM373-3p | TCACTTGATCAGCACGCCGAT (SEQ ID NO: 47) |
| 5 | Bm419 | Bmpde-2 | BM419-5p | ATGTACAACGACGAGAGCGTG (SEQ ID NO: 48) | BM419-3p | TCAGCCCAGGTCCCGCTCCG (SEQ ID NO: 49) |
| 6 | Bm499 | WbHypothetical | BM499-5p | ATGAGCACCCTGGAGAACGCC (SEQ ID NO: 50) | BM499-3p | TCAGCACAGGTTGATGGTGCA (SEQ ID NO: 51) |
| 7 | Bm698 | Bm-wnk-1 | BM698-5p | ATGCTGAAGGGCCTGCAGCAC (SEQ ID NO: 52) | BM698-3p | TCAGCTCTCGCCCGGTCACCAT (SEQ ID NO: 53) |
| 8 | Bm827 | BmHypothetical | BM827-5p | ATGACCCTGGCCATCGGCGCC (SEQ ID NO: 54) | BM827-3p | TCAGAAGGGCTGCCGCTCGTT (SEQ ID NO: 55) |
| 9 | Bm97 | BmEpicuticulin | BM97-5p | CTGCACAAGCACAACGCCCAC (SEQ ID NO: 56) | BM97-3p | TCACTGCCAGTTCTGCAGCTG (SEQ ID NO: 57) |

FIGURE 6B

|    | Plasmid Name | Name | Fwd Primer Name | Sequence Specific Forward Primer | Rev Primer Name | Sequence Specific Reverse Primer |
|----|---|---|---|---|---|---|
| 10 | Wb123 | WbSerpin | WB123-5p | ATCCTGGGCCAGATCAGCCTG (SEQID NO: 58) | WB123-3p | TCACTTCACGAACTGGCCGAT (SEQID NO: 59) |
| 11 | Wb126 | WbHypothetical | WB126-5p | CGGAGCCCCGGCATCGAGGGC (SEQID NO: 60) | WB126-3p | TCAGTAGCCGGGGGGGGGTCCG (SEQID NO: 61) |
| 12 | Wb132 | WbEndochitinase | WB132-5p | ATGAAGAGCGCCTTCGTGGAG (SEQID NO: 62) | WB132-3p | TCAGGTGGGCAGCTCGGGGTT (SEQID NO: 63) |
| 13 | Wb153 | WbHypothetical | WB153-5p | ATGCCCTTCCTGTTCTGCGAC (SEQID NO: 64) | WB153-3p | TCACTGCTTGTAGGGCAGCCT (SEQID NO: 65) |
| 14 | Wb261 | WbHypothetical | WB261-5p | ATGTGCACCGACGCCAACAGC (SEQID NO: 66) | WB261-3p | TCAGTTGTTCTTGTTCACGAT (SEQID NO: 67) |
| 15 | Wb267 | WbHypothetical | WB267-5p | ATGAACAGCCAGACCGAGACC (SEQID NO: 68) | WB267-3p | TCACTCGGTCAGGGTGATGAA (SEQID NO: 69) |
| 16 | Wb289 | WbHypothetical | WB289-5p | TTCGAGACCTGCGTGGACAAG (SEQID NO: 70) | WB289-3p | TCAGTGCACCTGCTCGTTCAT (SEQID NO: 71) |
| 17 | Wb352 | WbHypothetical | WB352-5p | ATGGTGACCATCGTGAGCAAG (SEQID NO: 72) | WB352-3p | TCAGTTGCCGATGCCGTCCTC (SEQID NO: 73) |
| 18 | Wb443 | WbHypothetical | WB443-5p | ATGCTGGCCGAGATCAGCAGC (SEQID NO: 74) | WB443-3p | TCACAGCTTGGGCCGGCTCAT (SEQID NO: 75) |
| 19 | Wb610 | Wbpat-6 | WB610-5p | ATGCCCTTCCTGTTCTGCGAC (SEQID NO: 76) | WB610-3p | TCACTGCTTGTAGGGCAGCCT (SEQID NO: 77) |

SEQUENCE LISTING

```
<160> NUMBER OF SEQ ID NOS: 77

<210> SEQ ID NO 1
<211> LENGTH: 1116
<212> TYPE: DNA
<213> ORGANISM: Artificial Sequence
<220> FEATURE:
<223> OTHER INFORMATION: Synthetic

<400> SEQUENCE: 1
atcctgggcc agatcagcct gaccgaccgg gcccagctgg acttcgccgt gaacctgctg        60
cagaacgtgg ccgagagcga ccggagcagc atcctgagcc ccttcagcgt gagcaccagc       120
ctgttcatcg cctacctggc agcagacgga gagaccaagc agcagctgca gaacgcactg       180
ggcaagaccg caagcaccag ccagttcaga atccacttcg ccaagcagct ggcctacctg       240
gcccgggccg agagccggaa ctacaccctg aacgtggcca accggttcta cgtgcgggag       300
gagttcagca ccaaggagag cttccagcgg gtgctgagct tctactacaa cgagatcctg       360
tacaagttca acttcgagca gcggaacgag ctggtgcagg agatcaacga ctgggtgagc       420
aacgagacca caacaaggt gaccaagatg atcaccgaga acagcatcac cgaggacacc       480
cggatgctgc tgatgaacgc catccacttc aagggcacct ggaccaccca gttcatcgac       540
ttcgtgacca gcagaagca gttccacatc agcgagaacg aggtgaagct ggtgcccatg       600
atggccaaga cgacaccgt gcctactac gaggacgacg tggtgaaagt gatcaagctg       660
ccctacaccg gaggagaggt ggagatggtg gtcatcctgc caaagcggcg gttcggactg       720
agcgacgtgc tgaagaacct gagcggcgag aagctgctga gtacgtgaa cgaggccaag       780 aaccggaccg tgagcatccg gatgcccgg ttccaggtgg aggagaagcg gaacctgaac       840
aacgccctgc aggccatcgg catcaccgac gccttcagcg gcaaggccga cttcggcgag       900
```

```
ctgctgaaca acagcatccc catcagcatc ggcaagatca tccacgccgg cttcatcgag      960
gtgaacgaga agggcaccga gagcgccgca gccaccctga tcgagctgga ggacaggatg     1020
gcaagcagcc ggaacttcaa cgccgacgag cccttcctgt tcgccatcgt gaaggacctg     1080
aagaccgtgc tgttcatcgg ccagttcgtg aagtga                              1116

<210> SEQ ID NO 2
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward Primer.

<400> SEQUENCE: 2
gagggatcca tgccactgat gtaccagtac                                        30

<210> SEQ ID NO 3
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse Primer.

<400> SEQUENCE: 3
gagctcgagt cagcagaagg tcttggcgat                                        30

<210> SEQ ID NO 4
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward Primer.

<400> SEQUENCE: 4
gagggatcca tgttcctgca gaagaaggac                                        30

<210> SEQ ID NO 5
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse Primer.

<400> SEQUENCE: 5
gagctcgagt cacagcagcc gctgctgcca                                        30

<210> SEQ ID NO 6
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward Primer.
```

<400> SEQUENCE: 6
gagggatcca tgaccagccg gcaccggcac                                30

<210> SEQ ID NO 7
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse Primer.

<400> SEQUENCE: 7
gagctcgagt cagtcgaagc acaggttcag                                30

<210> SEQ ID NO 8
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward Primer.

<400> SEQUENCE: 8
gagggatcca gccagaacta cgtgctggag                                30

<210> SEQ ID NO 9
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse Primer.

<400> SEQUENCE: 9
gagctcgagt cacttgatca gcacgccgat                                30

<210> SEQ ID NO 10
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward Primer.

<400> SEQUENCE: 10
gagggatcca tgtacaacga cgagagcgtg                                30

<210> SEQ ID NO 11
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse Primer.

<400> SEQUENCE: 11
gagctcgagt cagcccaggt cccgctcccg                                30

<210> SEQ ID NO 12
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward Primer.

<400> SEQUENCE: 12
gagggatcca tgagcaccct ggagaacgcc                                          30

<210> SEQ ID NO 13
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse Primer.

<400> SEQUENCE: 13
gagctcgagt cagcacaggt tgatggtgca                                          30

<210> SEQ ID NO 14
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward Primer.

<400> SEQUENCE: 14
gagggatcca tgctgaaggg cctgcagcac                                          30

<210> SEQ ID NO 15
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse Primer.

<400> SEQUENCE: 15
gagctcgagt cagctctcgc cggtcaccat                                          30

<210> SEQ ID NO 16
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward Primer.

<400> SEQUENCE: 16
gagggatcca tgaccctggc catcggcgcc                                          30

-continued

```
<210> SEQ ID NO 17
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse Primer.

<400> SEQUENCE: 17
gagctcgagt cagaagggct gccgctcgtt                                    30

<210> SEQ ID NO 18
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward Primer.

<400> SEQUENCE: 18
gagggatccc tgcacaagca caacgcccac                                    30

<210> SEQ ID NO 19
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse Primer.

<400> SEQUENCE: 19
gagctcgagt cactgccagt tctgcagctg                                    30

<210> SEQ ID NO 20
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward Primer.

<400> SEQUENCE: 20
gagggatcca tcctgggcca gatcacctg                                     29

<210> SEQ ID NO 21
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse Primer.

<400> SEQUENCE: 21
gagctcgagt cacttcacga actggccgat                                    30

<210> SEQ ID NO 22
<211> LENGTH: 30
<212> TYPE: DNA
<213> ORGANISM: Artificial Sequence
```

```
<220> FEATURE:
<223> OTHER INFORMATION: Synthetic
<220> FEATURE:
<221> NAME/KEY: misc_feature
<223> OTHER INFORMATION: Forward Primer.

<400> SEQUENCE: 22
gagggatccc ggagccccgg catcgagggc                                              30

<210> SEQ ID NO 23
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse Primer.

<400> SEQUENCE: 23
gagctcgagt cagtagccgg gggcggtccg                                              30

<210> SEQ ID NO 24
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward Primer.

<400> SEQUENCE: 24
gagggatcca tgaagagcgc cttcgtggag                                              30

<210> SEQ ID NO 25
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse Primer.

<400> SEQUENCE: 25
gagctcgagt caggtgggca gctcggggtt                                              30

<210> SEQ ID NO 26
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward Primer.

<400> SEQUENCE: 26
gagggatcca tgcccttcct gttctgcgac                                              30

<210> SEQ ID NO 27
<211> LENGTH: 30
<212> TYPE: DNA
<213> ORGANISM: Artificial Sequence
<220> FEATURE:
<223> OTHER INFORMATION: Synthetic
```

-continued

<220> FEATURE:
<221> NAME/KEY: misc_feature
<223> OTHER INFORMATION: Reverse Primer.

<400> SEQUENCE: 27
gagctcgagt cactgcttgt agggcagcct                                                30

<210> SEQ ID NO 28
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward Primer.

<400> SEQUENCE: 28
gagggatcca tgtgcaccga cgccaacagc                                                30

<210> SEQ ID NO 29
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse Primer.

<400> SEQUENCE: 29
gagctcgagt cagttgttct tgttcacgat                                                30

<210> SEQ ID NO 30
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward Primer.

<400> SEQUENCE: 30
gagggatcca tgaacagcca gaccgagacc                                                30

<210> SEQ ID NO 31
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse Primer.

<400> SEQUENCE: 31
gagctcgagt cactcggtca gggtgatgaa                                                30

<210> SEQ ID NO 32
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward Primer.

<400> SEQUENCE: 32
gagggatcct tcgagacctg cgtggacaag                               30

<210> SEQ ID NO 33
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse Primer.

<400> SEQUENCE: 33
gagctcgagt cagtgcacct gctcgttcat                               30

<210> SEQ ID NO 34
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward Primer.

<400> SEQUENCE: 34
gagggatcca tggtgaccat cgtgagcaag                               30

<210> SEQ ID NO 35
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse Primer.

<400> SEQUENCE: 35
gagctcgagt cagttgccga tgccgtcctc                               30

<210> SEQ ID NO 36
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward Primer.

<400> SEQUENCE: 36
gagggatcca tgctggccga gatcagcagc                               30

<210> SEQ ID NO 37
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse Primer.

<400> SEQUENCE: 37
gagctcgagt cacagcttgg gccggctcat                               30

```
<210> SEQ ID NO 38
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward Primer.

<400> SEQUENCE: 38
gagggatcca tgcccttcct gttctgcgac                                              30

<210> SEQ ID NO 39
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse Primer.

<400> SEQUENCE: 39
gagctcgagt cactgcttgt agggcagcct                                              30

<210> SEQ ID NO 40
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward Primer.

<400> SEQUENCE: 40
atgccactga tgtaccagta c                                                       21

<210> SEQ ID NO 41
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse Primer.

<400> SEQUENCE: 41
tcagcagaag gtcttggcga t                                                       21

<210> SEQ ID NO 42
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward Primer.

<400> SEQUENCE: 42
atgttcctgc agaagaagga c                                                       21

<210> SEQ ID NO 43
<211> LENGTH: 21
<212> TYPE: DNA
<213> ORGANISM: Artificial Sequence
```

-continued

```
<220> FEATURE:
<223> OTHER INFORMATION: Synthetic
<220> FEATURE:
<221> NAME/KEY: misc_feature
<223> OTHER INFORMATION: Reverse Primer.

<400> SEQUENCE: 43
tcacagcagc cgctgctgcc a                                              21

<210> SEQ ID NO 44
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward Primer.

<400> SEQUENCE: 44
atgaccagcc ggcaccggca c                                              21

<210> SEQ ID NO 45
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse Primer.

<400> SEQUENCE: 45
tcagtcgaag cacaggttca g                                              21

<210> SEQ ID NO 46
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward Primer.

<400> SEQUENCE: 46
agccagaact acgtgctgga g                                              21

<210> SEQ ID NO 47
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse Primer.

<400> SEQUENCE: 47
tcacttgatc agcacgccga t                                              21

<210> SEQ ID NO 48
<211> LENGTH: 21
<212> TYPE: DNA
<213> ORGANISM: Artificial Sequence
<220> FEATURE:
<223> OTHER INFORMATION: Synthetic
```

```
<220> FEATURE:
<221> NAME/KEY: misc_feature
<223> OTHER INFORMATION: Forward Primer.

<400> SEQUENCE: 48
atgtacaacg acgagagcgt g                                               21

<210> SEQ ID NO 49
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse Primer.

<400> SEQUENCE: 49
tcagcccagg tcccgctccc g                                               21

<210> SEQ ID NO 50
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward Primer.

<400> SEQUENCE: 50
atgagcaccc tggagaacgc c                                               21

<210> SEQ ID NO 51
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse Primer.

<400> SEQUENCE: 51
tcagcacagg ttgatggtgc a                                               21

<210> SEQ ID NO 52
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward Primer.

<400> SEQUENCE: 52
atgctgaagg gcctgcagca c                                               21

<210> SEQ ID NO 53
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse Primer.
```

<400> SEQUENCE: 53
tcagctctcg ccggtcacca t                                          21

<210> SEQ ID NO 54
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward Primer.

<400> SEQUENCE: 54
atgaccctgg ccatcggcgc c                                          21

<210> SEQ ID NO 55
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse Primer.

<400> SEQUENCE: 55
tcagaagggc tgccgctcgt t                                          21

<210> SEQ ID NO 56
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward Primer.

<400> SEQUENCE: 56
ctgcacaagc acaacgccca c                                          21

<210> SEQ ID NO 57
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse Primer.

<400> SEQUENCE: 57
tcactgccag ttctgcagct g                                          21

<210> SEQ ID NO 58
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward Primer.

<400> SEQUENCE: 58
atcctgggcc agatcagcct g                                          21

```
<210> SEQ ID NO 59
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse Primer.

<400> SEQUENCE: 59
tcacttcacg aactggccga t                                              21

<210> SEQ ID NO 60
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward Primer.

<400> SEQUENCE: 60
cggagccccg gcatcgaggg c                                              21

<210> SEQ ID NO 61
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse Primer.

<400> SEQUENCE: 61
tcagtagccg ggggcggtcc g                                              21

<210> SEQ ID NO 62
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward Primer.

<400> SEQUENCE: 62
atgaagagcg ccttcgtgga g                                              21

<210> SEQ ID NO 63
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse Primer.

<400> SEQUENCE: 63
tcaggtgggc agctcggggt t                                              21

<210> SEQ ID NO 64
<211> LENGTH: 21
<212> TYPE: DNA
<213> ORGANISM: Artificial Sequence
```

```
<220> FEATURE:
<223> OTHER INFORMATION: Synthetic
<220> FEATURE:
<221> NAME/KEY: misc_feature
<223> OTHER INFORMATION: Forward Primer.

<400> SEQUENCE: 64
atgcccttcc tgttctgcga c                                              21

<210> SEQ ID NO 65
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse Primer.

<400> SEQUENCE: 65
tcactgcttg tagggcagcc t                                              21

<210> SEQ ID NO 66
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward Primer.

<400> SEQUENCE: 66
atgtgcaccg acgccaacag c                                              21

<210> SEQ ID NO 67
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse Primer.

<400> SEQUENCE: 67
tcagttgttc ttgttcacga t                                              21

<210> SEQ ID NO 68
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward Primer.

<400> SEQUENCE: 68
atgaacagcc agaccgagac c                                              21

<210> SEQ ID NO 69
<211> LENGTH: 21
<212> TYPE: DNA
<213> ORGANISM: Artificial Sequence
<220> FEATURE:
<223> OTHER INFORMATION: Synthetic
```

```
<220> FEATURE:
<221> NAME/KEY: misc_feature
<223> OTHER INFORMATION: Reverse Primer.

<400> SEQUENCE: 69
tcactcggtc agggtgatga a                                              21

<210> SEQ ID NO 70
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward Primer.

<400> SEQUENCE: 70
ttcgagacct gcgtggacaa g                                              21

<210> SEQ ID NO 71
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse Primer.

<400> SEQUENCE: 71
tcagtgcacc tgctcgttca t                                              21

<210> SEQ ID NO 72
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward Primer.

<400> SEQUENCE: 72
atggtgacca tcgtgagcaa g                                              21

<210> SEQ ID NO 73
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse Primer.

<400> SEQUENCE: 73
tcagttgccg atgccgtcct c                                              21

<210> SEQ ID NO 74
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward Primer.
```

-continued

```
<400> SEQUENCE: 74
atgctggccg agatcagcag c                                              21

<210> SEQ ID NO 75
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse Primer.

<400> SEQUENCE: 75
tcacagcttg ggccggctca t                                              21

<210> SEQ ID NO 76
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward Primer.

<400> SEQUENCE: 76
atgcccttcc tgttctgcga c                                              21

<210> SEQ ID NO 77
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse Primer.

<400> SEQUENCE: 77
tcactgcttg tagggcagcc t                                              21
```

DIAGNOSTIC ASSAYS AND METHODS OF USE FOR DETECTION OF FILARIAL INFECTION

CROSS-REFERENCE TO RELATED APPLICATION

This patent application is the U.S. national phase of International Patent Application No. PCT/US2011/058561, filed Oct. 31, 2011, which claims the benefit of U.S. Provisional Patent Application No. 61/410,239, filed Nov. 4, 2010, the entire contents of which are incorporated by reference.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 20,050 Byte ASCII (Text) file named "712635ST25.TXT," dated Apr. 11, 2013.

BACKGROUND OF THE INVENTION

*Wuchereria bancrofti*, the major causative organism of lymphatic filariasis (LF), is a filarial nematode estimated to infect 120 million people worldwide, with an additional billion people felt to be at risk for infection. *Wuchereria bancrofti* is a vector-borne parasite that has a complex lifecycle that begins when the infective larvae stage (L3) are deposited on the skin. These L3 develop in the human (over a six month period) to adults living in lymphatics where they mate and produce microfilariae that circulate in the blood and which ultimately get picked up by new vectors to complete the lifecycle. The period between infection and when the microfilariae appear is called the prepatent period and it is during this period when standard diagnostics are not useful.

Among the neglected tropical diseases (NTDs), lymphatic filariasis is one that has been targeted for elimination by 2020 using mass drug administration (MDA) to interrupt transmission of this mosquito borne infection. As part of this effort, based on yearly administration of two antifilarial drugs, methods for detecting infection during the prepatent period is necessary both to detect infection on an individual basis and to detect early recrudescence once MDA is instituted. Moreover, methods to be used to certify areas free of infection will also be necessary. To date, the antigens used to base assays, such as Bm-14, have suffered from complete cross-reaction with *Brugia malayi* (a related filarial parasite) and also from significant cross-reaction with other filarial parasites such as *Loa loa, Mansonella perstans*, and *Onchocerca volvulus* (the causative agent of onchocerciasis), whose geographic distribution often overlaps with that of *Wuchereria bancrofti*. Thus, given the potential for the serious, disabling disease associated with *Wuchereria bancrofti* and *Brugia malayi* infection, there is a need both to detect infection early following exposure to infective mosquitoes, and to certify areas free from infection, there remains a need for new methods of diagnosis to detect *Wuchereria bancrofti* and *Brugia malayi*.

BRIEF SUMMARY OF THE INVENTION

In accordance with an embodiment of the invention, an L3- and LF-specific antigen is identified that can be used as a rapid, high throughput, and specific tool to not only diagnose individuals with *Wuchereria bancrofti* and *Brugia malayi* infections, but also as a sensitive and point-of care method for early detection of recrudescent infections in areas of control and for mapping new areas of transmission of *Wuchereria bancrofti* and/or *Brugia malayi* infection.

According to an embodiment of the invention, an isolated antigen from *Wuchereria bancrofti* (*W. bancrofti*) infective larvae (L3) is provided, comprising the *W. bancrofti* immunoreactive antigen Wb123.

In an embodiment, the invention provides a polynucleotide which encodes the Wb123 antigen, the polynucleotide comprising SEQ ID NO: 1.

In an alternate embodiment the invention provides a polynucleotide which is complementary to the polynucleotide provided as SEQ ID NO: 1.

In another embodiment, the invention provides a Wb123 polypeptide encoded by the polynucleotide of SEQ ID NO: 1.

In another embodiment, the invention provides a composition comprising the polynucleotide of SEQ ID NO: 1, and a pharmaceutically acceptable carrier.

In yet another embodiment, the invention provides for a composition comprising the polypeptide encoded by the polynucleotide of SEQ ID NO: 1, and a pharmaceutically acceptable carrier.

In another embodiment, the invention provides a method for detecting the presence of antibodies to a protein in *Wuchereria bancrofti* or *Brugia malayi* infective larvae (L3) in a sample, the method comprising: a) contacting the sample with a first binding reagent which comprises a fusion protein having a reporter domain and a binding domain, the binding domain comprising the Wb123 antigen or a functional portion thereof; b) contacting the immunocomplex of a) with an immobilized second binding reagent, the second reagent capable of binding the antibodies if present in the sample and forming an immunocomplex, the first and second binding reagents being capable of binding the antibodies simultaneously if present in the sample, such that the first binding reagent becomes immobilized through the antibodies bound to the second binding reagent; c) detecting whether the first binding reagent has become immobilized to thereby detect the presence or concentration of the antibodies; and d) correlating the detection of the analyte with the presence of antibodies resulting from *Wuchereria bancrofti* or *Brugia malayi* infection in the sample.

In accordance with the present invention, the reporter domain, in an embodiment, comprises *Renilla* luciferase, the first binding reagent comprises a Ruc-Wb123 construct, the second binding reagent comprises protein A/G, and the reporter domain substrate comprises colenterazine.

In an embodiment, the present invention provides a method for detecting exposure to *Wuchereria bancrofti* or *Brugia malayi* in a subject comprising: a) obtaining a sample from a subject suspected of being exposed to *W. bancrofti* or *B. malayi*; b) contacting the sample of a) with a mixture comprising a *Renilla* luciferase fusion protein comprising the Wb123 antigen to create an immunocomplex; c) contacting the resulting immunocomplex of b) with a protein A/G binding substrate and allowing the protein A/G binding substrate to bind to the immunocomplex; d) removing any unbound protein A/G binding substrate; e) contacting the resulting immunocomplex from d) with a luciferase substrate and incubating the mixture under conditions suitable to produce luminescence; f) measuring the luminescence produced in the sample; and g) correlating the luminescence produced with exposure to *Wuchereria bancrofti* or *Brugia malayi*.

In yet another embodiment, the present invention provides a recombinant expression vector comprising the polynucleotide sequence of SEQ ID NO: 1. Preferably, the expression vector comprises the vector pREN2.

In an embodiment, the present invention provides an isolated host cell comprising the recombinant expression vector comprising the polynucleotide sequence of SEQ ID NO: 1. Preferably the host cell is a COS1 cell.

In a further embodiment, the present invention provides a population of cells comprising at least one host cell comprising a COS1 cell containing the recombinant expression vector comprising the polynucleotide sequence of SEQ ID NO: 1.

In an embodiment, the present invention provides a method for detecting the quantity of a specific immunoglobulin antibody to Wb123 in a sample, the method comprising: (a) providing the Wb123 antigen which selectively forms a first immunocomplex with a sample antibody, the Wb123 antigen being directly bound to a solid support at a first location; (b) providing an antibody which selectively forms a second immunocomplex with a sample antigen, the antibody being directly bound to the solid support at a second location; (c) contacting the first location on the solid support with at least a portion of a biological sample under conditions whereby the first immunocomplex can form and contacting the second location on the solid support with at least a portion of the sample under conditions whereby the second immunocomplex can form; (d) washing unbound material from the first location and from the second location; (e) separately detecting whether the first immunocomplex is formed and whether the second immunocomplex is formed, the first immunocomplex being detected with a labeled antigen which selectively binds to the first complex and the second immunocomplex being detected by adding a labeled antibody which selectively binds to the second immunocomplex, the labeled antibody being presented to both the first and the second locations; and f) correlating the detection of the amount of labeled antibody being presented to both the first and the second locations with the amount of specific immunoglobulin antibody to Wb123 antibody in the sample. In accordance with the present invention, the specific immunoglobulin can be IgG and IgE.

BRIEF DESCRIPTION OF THE SEVERAL VIEWS OF THE DRAWING(S)

FIG. 1 is the nucleotide sequence of the Wb123 antigen polypeptide (SEQ ID NO: 1).

FIG. 2 shows a schematic describing a luciferase immunoprecipitation system (LIPS) assay. A Ruc-Wb123 fusion protein expression product is provided in a multiwell plate. Patient serum is added and an immune complex forms between the Wb123 antigen and the *Wuchereria bancrofti* or *Brugia malayi* infective larvae (L3) mf antibodies in the serum. After a period of incubation, a suspension of protein A/G beads in phosphate-buffered saline is added to the bottom of a 96-well filter high-throughput-screening plate. The immune complex is then added to the protein A/G beads, incubated and washed. The luminescence substrate and reactant is then added to the complex and the luminescence is measured in a plate reader.

FIG. 3 is a graph depicting the results of a LIPS assay which shows order of magnitude specificity for antibodies to *Wuchereria bancrofti* or *Brugia malayi* over normal sera and sera from patients infected with other filarial diseases such as *Loa loa* and *Onchocerca volvulus*. Antibody responses to Wb123 show minimal cross reactivity with other filarial infections. The abbreviations MF+ and CG+ mean microfilaria positive and circulating antigen positive, respectively.

FIG. 4 depicts the results of a LIPS assay with a blinded study. Antibodies to Wb123 unequivocally differentiate between *W. bancrofti* infected individuals and non-filarial infected individuals (controls). The abbreviation MF pos means microfilaria positive.

FIGS. 5A and 5B are tables depicting the 19 potential antigen targets identified from ESTs and the specific primers initially used to amplify and clone the targets.

FIGS. 6A and 6B are tables depicting a second set of primers used to specifically amplify the DNA either from the pREN2 vector or for sequencing.

DETAILED DESCRIPTION OF THE INVENTION

Figure 2:
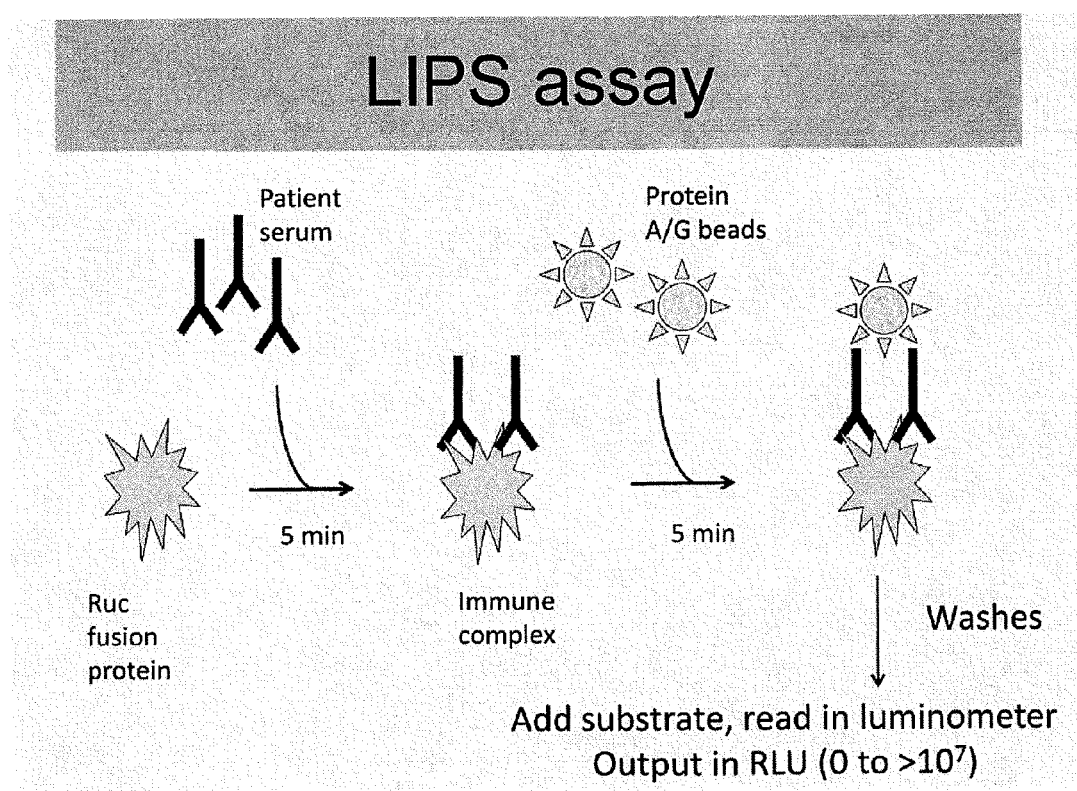

A new approach to immunologically-based assay development has identified species and stage-specific transcripts, using tools to analyze and organize expressed sequence tags (ESTs) generated from and *Wuchereria bancrofti, Brugia malayi* and other filarial organisms. From 20 identified *Wuchereria bancrofti* larval-specific and species specific transcripts, one antigen polypeptide termed Wb123, met all the criteria for being used for early detection of *Wuchereria bancrofti* and *Brugia malayi* infection. In immunologically based assays (using either detection of IgG or IgG4 antibodies), the assays as configured detects *Wuchereria bancrofti* and *Brugia malayi* infection specifically with no cross reactivity with the closely related other filariae, nor with other control sera (normals, uninfected patients with high levels of IgE or peripheral blood eosinophilia, patients with autoimmune diseases and non-filarial parasitic infections).

In accordance with the present invention, a bioinformatics approach was used to determine potential antigens that could be used for LF-specific antibodies. *Renilla* luciferase (Ruc)-antigen fusions were then produced in Cos1 cells for use in an immunoprecipitation assay called LIPS (denoting luciferase immunoprecipitation systems) to measure antibody responses. The results of the present invention show that a L3- and LF-specific antigen was identified that can be used as a rapid, high throughput, and specific tool to not only diagnose individual *Wuchereria bancrofti* and *Brugia malayi* infections, but also as a sensitive and point-of care method for early detection of recrudescent infections in areas of control and for mapping new areas of transmission of *Wuchereria bancrofti* and/or *Brugia malayi* infection.

According to an embodiment of the invention, an isolated antigen from *Wuchereria bancrofti* (*W. bancrofti*) infective larvae (L3) is provided, comprising the *W. bancrofti* immunoreactive antigen Wb123.

In an embodiment, the invention provides a polynucleotide which encodes the Wb123 antigen, the polynucleotide comprising SEQ ID NO: 1.

In an alternate embodiment the invention provides a polynucleotide which is complementary to the polynucleotide provided as SEQ ID NO: 1.

In another embodiment, the invention provides a Wb123 polypeptide encoded by the polynucleotide of SEQ ID NO: 1.

In another embodiment, the invention provides a composition comprising the polynucleotide of SEQ ID NO: 1, and a pharmaceutically acceptable carrier.

In yet another embodiment, the invention provides for a composition comprising the polypeptide encoded by the polynucleotide of SEQ ID NO: 1, and a pharmaceutically acceptable carrier.

In another embodiment, the invention provides a method for detecting the presence of antibodies to a protein in *Wuchereria bancrofti* or *Brugia malayi* infective larvae (L3) in a sample, the method comprising: a) contacting the sample with a first binding reagent which comprises a fusion protein having a reporter domain and a binding domain, the binding domain comprising the Wb123 antigen or a functional portion thereof; b) contacting the immunocomplex of a) with an immobilized second binding reagent, the second reagent capable of binding the antibodies if present in the sample and forming an immunocomplex, the first and second binding reagents being capable of binding the antibodies simultaneously if present in the sample, such that the first binding reagent becomes immobilized through the antibodies bound to the second binding reagent; c) detecting whether the first binding reagent has become immobilized to thereby detect the presence or concentration of the antibodies; and d) correlating the detection of the analyte with the presence of antibodies resulting from *Wuchereria bancrofti* or *Brugia malayi* infection in the sample.

In accordance with the present invention, the reporter domain, in an embodiment, comprises *Renilla* luciferase, the first binding reagent comprises a Ruc-Wb123 construct, the second binding reagent comprises protein A/G, and the reporter domain substrate comprises colenterazine.

In an embodiment, the present invention provides a method for detecting exposure to *Wuchereria bancrofti* or *Brugia malayi* in a subject comprising: a) obtaining a sample from a subject suspected of being exposed to *W. bancrofti* or *B. malayi*; b) contacting the sample of a) with a mixture comprising a *Renilla* luciferase fusion protein comprising the Wb123 antigen to create an immunocomplex; c) contacting the resulting immunocomplex of b) with a protein A/G binding substrate and allowing the protein A/G binding substrate to bind to the immunocomplex; d) removing any unbound protein A/G binding substrate; e) contacting the resulting immunocomplex from d) with a luciferase substrate and incubating the mixture under conditions suitable to produce luminescence; f) measuring the luminescence produced in the sample; and g) correlating the luminescence produced with exposure to *Wuchereria bancrofti* or *Brugia malayi*.

In yet another embodiment, the present invention provides a recombinant expression vector comprising the polynucleotide sequence of SEQ ID NO: 1. Preferably, the expression vector comprises the vector pREN2.

In an embodiment, the present invention provides an isolated host cell comprising the recombinant expression vector comprising the polynucleotide sequence of SEQ ID NO: 1. Preferably the host cell is a COS1 cell.

In a further embodiment, the present invention provides a population of cells comprising at least one host cell comprising a COS1 cell containing the recombinant expression vector comprising the polynucleotide sequence of SEQ ID NO: 1.

In an embodiment, the present invention provides a method for detecting the quantity of a specific immunoglobulin antibody to Wb123 in a sample, the method comprising: (a) providing the Wb123 antigen which selectively forms a first immunocomplex with a sample antibody, the Wb123 antigen being directly bound to a solid support at a first location; (b) providing an antibody which selectively forms a second immunocomplex with a sample antigen, the antibody being directly bound to the solid support at a second location; (c) contacting the first location on the solid support with at least a portion of a biological sample under conditions whereby the first immunocomplex can form and contacting the second location on the solid support with at least a portion of the sample under conditions whereby the second immunocomplex can form; (d) washing unbound material from the first location and from the second location; (e) separately detecting whether the first immunocomplex is formed and whether the second immunocomplex is formed, the first immunocomplex being detected with a labeled antigen which selectively binds to the first complex and the second immunocomplex being detected by adding a labeled antibody which selectively binds to the second immunocomplex, the labeled antibody being presented to both the first and the second locations; and f) correlating the detection of the amount of labeled antibody being presented to both the first and the second locations with the amount of specific immunoglobulin antibody to Wb123 antibody in the sample. In accordance with the present invention, the specific immunoglobulin can be IgG and IgE.

It is also understood that the sample can be from a mammal, and for example, from a human. If the sample is from a human, it can be any type of sample, including blood, serum, plasma, sputum, lymph, saliva, and the like. Preferably the sample is a human serum sample.

The isolated or purified polypeptides, and proteins of the invention (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

When the isolated or purified polypeptides and proteins of the invention (including functional portions and functional variants) are in the form of a salt, preferably, the polypeptides are in the form of a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

The isolated or purified polypeptides, and/or proteins of the invention (including functional portions and functional variants thereof) can be obtained by methods known in the art. Suitable methods of de novo synthesizing polypeptides and proteins are described in references, such as Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; *Epitope Mapping*, ed. Westwoood et al., Oxford University Press, Oxford, United Kingdom, 2001; and U.S. Pat. No. 5,449,752. Also, polypeptides and proteins can be recombinantly produced using the nucleic acids described herein using standard recombinant methods. See, for instance, Sambrook et al., *Molecular Cloning: A Laboratory Manual*, 3$^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 2007. Further, some of the polypeptides, and proteins of the invention (including functional portions and functional variants thereof) can be isolated and/or purified from a source, such as a plant, a bacterium, an insect, a mammal, e.g., a rat, a mouse, a human, etc. Methods of isolation and purification are well-known in the art. Alternatively, the polypeptides, and/or proteins described herein (including functional portions and functional variants thereof) can be commercially synthesized by companies, such as Synpep (Dublin, Calif.), Peptide Technologies Corp. (Gaithersburg, Md.), and Multiple Peptide Systems (San Diego, Calif.). In this respect, the inventive polypeptides, and proteins can be synthetic, recombinant, isolated, and/or purified.

Included in the scope of the invention are conjugates, e.g., bioconjugates, or fusion proteins comprising any of the inventive polypeptides, or proteins (including any of the functional portions or variants thereof), nucleic acids, recombinant expression vectors, host cells, populations of host cells, or antibodies, or antigen binding portions thereof. Conjugates, as well as methods of synthesizing conjugates in general, are known in the art (See, for instance, Hudecz, F.,

*Methods Mol. Biol.* 298: 209-223 (2005) and Kirin et al., *Inorg. Chem.* 44(15): 5405-5415 (2005)).

By "nucleic acid" as used herein includes "polynucleotide," "oligonucleotide," and "nucleic acid molecule," and generally means an isolated or purified polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions. Embodiments of nucleic acids according to the invention can comprise, consist, or consist essentially of, any of the disclosed sequences, complementary sequences, and SEQ ID NOs.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

Embodiments of the invention also provide an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The isolated or purified nucleic acids of the invention can be incorporated into a recombinant expression vector. In this regard, an embodiment of the invention provides recombinant expression vectors comprising any of the isolated or purified nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages do not hinder the transcription or replication of the vector.

The recombinant expression vector of the invention can be any suitable recombinant expression vector, and can be used to transform or transfect any suitable host. Suitable vectors include those designed for propagation and expansion or for expression or both, such as plasmids and viruses. The vector can be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM and pMAMneo (Clontech). Preferably, the recombinant expression vector is pREN2, a FLAG-epitope tagged mammalian expression vector (Burbelo, P. D. et al, *BMC Biotechnology*, 5:22 (2005)).

The recombinant expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColE1, 2μ plasmid, λ, SV40, bovine papilloma virus, and the like.

Another embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α *E. coli* cells, Chinese hamster ovarian cells, monkey VERO cells, COS cells, HEK293 cells, and the like.

For purposes of amplifying or replicating the recombinant expression vector, the host cell is preferably a eukaryotic cell, e.g., a COS1 cell.

Another embodiment of the invention further provides an antibody, or antigen binding portion thereof, which specifically binds to the Wb123 protein or isolated or purified peptide fragments thereof described herein. In one embodiment, the antibody, or antigen binding portion thereof, binds to an epitope or peptide fragment which contains any of the mutant amino acids which differ from the wild-type proteins. The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. Also, the antibody can have any level of affinity or avidity for the mutated portion of the Wb123 protein or peptide fragments thereof of the present invention, such that there is minimal cross-reaction with other peptides or proteins.

Functional portions encompass, for example, those parts of a Wb123 polypeptide or protein that retain the ability to specifically bind to antibodies made through exposure to, or infection with, *Wuchereria bancrofti* or *Brugia malayi* infective larvae (L3) mf. In reference to the parent Wb123 polypeptide or protein, the functional portion can comprise, for instance, about 10%, 25%, 30%, 50%, 68%, 80%, 90%, 95%, or more, of the parent Wb123 polypeptide or protein. The functional portion can comprise additional amino acids at the amino or carboxy terminus of the portion, or at both termini, which additional amino acids are not found in the amino acid sequence of the parent Wb123 polypeptide or protein. Desirably, the additional amino acids do not interfere with the ability to specifically bind to antibodies made through exposure to, or infection with, *Wuchereria bancrofti* or *Brugia malayi* infective larvae (L3) mf.

Methods of testing antibodies for the ability to bind to any functional portion of any of the Wb123 protein or isolated or purified peptide fragments thereof are known in the art and include any antibody-antigen binding assay, such as, for example, radioimmunoassay (RIA), ELISA, Western blot, immunoprecipitation, and competitive inhibition assays (see, e.g., Janeway et al., infra, and U.S. Patent Application Publication 2002/0197266 A1).

For purposes of the present invention, the term "functional portion thereof" also includes a peptide fragment of the Wb123 protein having fewer amino acids than the amount of amino acids encoded by the polynucleotide of SEQ ID NO: 1, and which elicits a specific antibody response to *Wuchereria bancrofti* and/or *Brugia malayi* without significant cross-reactivity to other filarial species.

Suitable methods of making antibodies are known in the art. For instance, standard hybridoma methods are described in, e.g., Köhler and Milstein, *Eur. J. Immunol.*, 5, 511-519 (1976), Harlow and Lane (eds.), *Antibodies: A Laboratory Manual*, CSH Press (1988), and C. A. Janeway et al. (eds.), *Immunobiology*, 5$^{th}$ Ed., Garland Publishing, New York, N.Y. (2001)). Alternatively, other methods, such as EBV-hybridoma methods (Haskard and Archer, *J. Immunol. Methods*, 74(2), 361-67 (1984), and Roder et al., *Methods Enzymol.*, 121, 140-67 (1986)), and bacteriophage vector expression systems (see, e.g., Huse et al., Science, 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1).

Phage display furthermore can be used to generate the antibodies of the present invention. In this regard, phage libraries encoding antigen-binding variable (V) domains of antibodies can be generated using standard molecular biology and recombinant DNA techniques (see, e.g., Sambrook et al. (eds.), *Molecular Cloning, A Laboratory Manual*, 3$^{rd}$ Edition, Cold Spring Harbor Laboratory Press, New York (2001)). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150).

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are well known in the art and are described in detail in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., *J. Mol. Biol.*, 235, 959-973 (1994).

Also, the antibody, or antigen binding portion thereof which binds Wb123, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

The Wb123 polypeptides, proteins, (including functional portions and functional variants thereof), nucleic acids, recombinant expression vectors, host cells (including populations thereof), and antibodies (including antigen binding portions thereof), can be isolated and/or purified. The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than 60%, 70% or 80%, or can be 100%.

With respect to the inventive method of detecting the Wb123 protein or functional portion thereof, or Wb123 nucleic acid molecules in a host, the sample of cells of the host can be a sample comprising whole cells, lysates thereof, or a fraction of the whole cell lysates, e.g., a nuclear or cytoplasmic fraction, a whole protein fraction, or a nucleic acid fraction.

For purposes of the inventive detecting method, the contacting can take place in vitro or in vivo with respect to the host. Preferably, the contacting is in vitro.

In an embodiment, the present invention measures the Wb123 antigen in a sample using luciferase immunoprecipitation technology (LIPS) as described in Burbelo, P. D., et al., *Biochem. Biophys. Res. Commun.*, 366:1-7 (2008); and in U.S. Patent Application 2007/0259336, and incorporated by reference herein.

The first binding reagent of the present invention comprises a fusion protein having a reporter domain and a binding domain. The fusion protein may be made by conventional cloning techniques. The fusion protein may be expressed in a wide range of cells, including mammalian, yeast and plant cells. In a preferred embodiment, the fusion protein is expressed in mammalian cells or cell extracts, such as Cos cells, HeLa, Vero, CHO, NIH 3T3, 293, etc. The use of mammalian cells is particularly preferred, and more preferably, COS1 cells.

In this regard, embodiments of the invention also provide a fusion protein comprising at least one of the inventive polypeptides described herein, for example, Wb123, along with at least one other polypeptide. The other polypeptide can exist as a separate polypeptide of the fusion protein, or can exist as a polypeptide, which is expressed in frame (in tandem) with one of the inventive polypeptides described herein. The other polypeptide can encode any peptidic or proteinaceous molecule, or a portion thereof, including, but not limited to an immunoglobulin, an enzyme, etc. The reporter domain of the first binding reagent comprises a detectable moiety that may be used to detect the presence of the first binding reagent. The detectable moiety may be any polypeptide or protein that is capable of detection, either directly or indirectly. Many such moieties are known. In a preferred embodiment, the detectable moiety is a detectable enzyme, such as luciferase, horseradish peroxidase, alkaline phosphatase, etc. *Renilla* luciferase is particularly preferred. In another embodiment, the detectable moiety comprises multiple copies of a detectable enzyme. Such may be accomplished by, for example, the use of a cloning vector coding for multiple copies of the enzyme, which may be linked in tandem, or located on either side of the binding domain. Other detectable moieties include, for example, fluorescent proteins such as green fluorescent protein, for example.

In an embodiment, the present invention provides a second binding reagent. The second binding reagent of the present invention should be capable of binding to the analyte of interest if present in the sample. The second binding reagent may comprise any moiety that is capable of binding to the analyte. Preferred moieties include proteins and antibodies. When the analyte is an antibody, the second binding reagent preferably comprises a protein known to bind to the class of such antibody, such as protein A or protein G, for example.

The second binding reagent of the present invention should also be immobilized. Many immobilization schemes are well known to one of skill in the art, and include covalent immobilization on a solid support such as plastics, magnetic beads, nylon, carbohydrate-based supports, etc. The second binding reagent may be immobilized at any time during the process. For example, it may be immobilized before contact with the fluid sample suspected of containing the analyte. In another embodiment, the second binding reagent may be immobilized after it is contacted with the analyte and/or the first binding reagent. In the latter embodiment, the binding reaction(s) is carried out in solution, then the second binding reagent is subsequently (or simultaneously) immobilized by methods well-known to one of ordinary skill. For example, the second binding reagent in solution may be contacted with a solid medium having an affinity for the second binding reagent, for example a bead coated with an antibody that binds to the second binding reagent.

Further, the first and second binding reagents should be capable of binding the analyte simultaneously if present in the sample. As used herein, the term "binding" is intended to mean any interaction or association between the second binding reagent and the analyte that will ultimately permit the analyte to be immobilized via the immobilized second binding reagent, and ultimately to immobilize the first binding reagent. Preferably the binding interaction will have a Kd of about $10^{-6}$, more preferably about $10^{-7}$, even more preferably about $10^{-8}$, and as high as about $10^{-14}$. In a preferred embodiment, such binding will be in the nature of a protein/protein or antigen/antibody interaction. When that occurs, it will be apparent that the first binding reagent becomes immobilized through the analyte and the second binding reagent. The binding domain of the first binding reagent may comprise a full-length protein, or a portion of a full-length protein sufficient to bind to the analyte.

It will be apparent that the analyte to be detected should be capable of binding simultaneously to the first and second binding reagents. In a preferred embodiment, the analyte is an antibody (e.g., an IgA, IgE, IgG, IgM, etc.), and the second binding reagent and the binding domain of the first binding reagent are both antigens. If the analyte is other than an antibody, then the second binding reagent and the binding domain of the first binding reagent may be antibodies that bind to the analyte.

The analyte to be detected may be indicative of the presence or progress of a disease state. For example, the present invention may be used detect the presence of antibodies generated in response to the presence of pathogens such as viruses, bacteria, fungi, parasites, etc. Any pathogen that generates a humoral response may be detected according to the present invention. In a preferred embodiment, the analyte may indicate the presence of microfilarial larvae or infection in a patient. In an embodiment, the analyte may indicate the presence of antibodies to *Wuchereria bancrofti* or *Brugia malayi* infective larvae (L3) microfilariae in a sample, and that a patient is infected with *Wuchereria bancrofti* or *Brugia malayii*.

The term "analyte" as used herein, means any antibody of binding fragment thereof which can specifically bind to the Wb123 antigen of the present invention or a functional portion thereof.

The LIPS assay used in embodiments of the methods of the present invention may be performed by contacting the first binding reagent with the sample and the second binding reagent. If the analyte is present, an immunocomplex is formed among the two binding reagents and the analyte. Because the second binding reagent is immobilized, the first binding reagent likewise becomes immobilized if the analyte is present. The immunocomplex is separated from the reaction mixture, for example by washing, and the presence of the first binding reagent in the complex is detected via the reporter domain. The presence (or concentration) of the first binding reagent in the immunocomplex is indicative of the presence (or concentration) of the analyte. The order of addition of the reagents and analyte is not critical. Thus, the analyte may be mixed with the first binding reagent, and then the second binding reagent may be added to the mixture. Alternatively, the steps could be reversed, i.e., the analyte may be mixed with the second binding reagent, and then the first binding reagent may be added to the mixture. Finally, the first and second binding reagents and the analyte could be mixed together at the same time, or the first and second binding reagents are pre-mixed and the analyte added to the mixture, forming the immunocomplex.

It will be apparent that the LIPS assay used in the method of the present invention may be carried out so as to detect a single analyte, e.g., by testing a sample with a single pair of binding reagents designed to detect a single analyte of interest, for example *Wuchereria bancrofti* or *Brugia malayi*. It is also contemplated that the present invention may be used to detect multiple analytes in a single sample. That may be done by utilizing multiple pairs of binding reagents designed to detect multiple analytes of interest. Such may be easily achieved by the use of, for example, multiple well plates, wherein the multiple first binding reagents are immobilized in discrete wells in the plate. Alternatively, multiple binding domains, each of which binds the different analytes, may be incorporated with the record binding reagent, for example, in tandem.

EXAMPLES

The following examples further illustrate the invention but, of course, should not be construed as in any way limiting its scope.

Example 1

Identification of Potential L3 Specific Antigen Targets. Expressed sequence tags (ESTs) from each of the available filariae were assembled into contigs using the Desktop cDNA Annotation System (dCAS 1.4.3) software package of Guo Y, et al., *Bioinformatics*, 25:1195-6 (2009). Contigs were selected for further evaluation as candidate assay targets based on the number of ESTs comprising the contig (abundance), length of at least 200 bp with a predicted open reading frame (ORF), and lack of sequence homology to i) the non-redundant protein database (nr), ii) ESTs from related filarial pathogens, and iii) Wb infective larvae (L3) ESTs. The results were used to identify those potential proteins that were specific for the lymphatic filariae *Wuchereria bancrofti* and/or *Brugia malayi*, and not expressed by related filariae *Loa loa*, *Onchocerca volvulus*. Nineteen potential candidates were selected. Each of the 19 was synthesized commercially (Genscript, Piscataway, N.J.). Using insert specific primers (FIG. 5) containing BamH1 and Xho1 modifications, each of these 19 DNA inserts were amplified and cloned into the BamH1/Xho1 site of pREN2, a mammalian Ruc expression vector described previously (Burbelo, P. D. et al., *BMC Biotechnol.*, 5:22 (2005)).

The primer linker sequences used to amplify one of the sequences, Wb123, from its pUC57 plasmid are as follows:

```
                                          (SEQ ID NO: 20)
Wb123fwd-5' GAGGGATCCATCCTGGGCCAGATCAGCCTG-3'
and
                                          (SEQ ID NO: 21)
Wb123rev-5' GAGCTCGAGTCACTTCACGAACTGGCCGAT-3'.
```

Example 2

Cloning and Protein Expression. Eighteen of the nineteen identified antigen target DNA sequences were cloned into a pREN vector for rapid protein expression in mammalian cells. pREN2, a mammalian *Renilla* luciferase (Ruc) expression vector was used to generate all plasmids according to the method of Burbelo et al. (2005). Inserts from each potential construct was amplified from an existing plasmid by PCR using gene-specific linker-primer adapters (FIG. 6). The gene-specific primer adapters for Wb123 were as follows: 5'-GAGG GATCCAATTCGGCACGAGCAGAA-3' (SEQ ID NO: 58) and 5'-GAGCTCGAGTTATTTTGGAC-GAAGTGC-3' (SEQ ID NO: 59). Following the polymerase chain reaction, the product was restricted with BamHI and XhoI and ligated into BamHI-XhoI cut pREN2. The resulting pREN2 expression vector was prepared using a Qiagen Midi kit (Qiagen, Gaithersburg, Md.). Automated DNA sequencing was used to confirm the integrity of the DNA constructs.

Example 3

Sera samples were collected from individuals seen under a variety of NIAID IRB approved research protocols in which Dr. Thomas Nutman was the Principal Investigator. Clinically proven samples of *Wucheria bancrofti* by microscopy and circulating antigen positivity using a commercially available TropBio™ kit that uses a monoclonal antibody (Og4C3) as the capture antibody.

Example 4

Antibody Reactivity Assessment. Eighteen expressed proteins were assessed for antibody reactivity using well-defined sera to insure specificity. Only 1/18 (Wb123) met the criteria for continued study and testing (data not shown).

Example 5

Wb 123 Amino Acid Sequence Analysis. Wb 123 comprises 372 amino acids, as assessed by MacVector™, Sequencher™, and Lasergene™ software. Based on the sequence analysis (NCBI BLAST), it may be an expressed protein in the serpin family of proteins, however it has little protein homology with human serpins. The sequence also has homology to serine protease inhibitors. It is also identified to be a known secreted product of filarial nematodes. Wb123 is typically immunogenic in humans.

Example 6

LIPS assays. Extracts containing the Ruc-Wb123 antigen fusions were prepared from transfected Cos1 cells, as previously described (Burbelo, P. D. et al. 2008). Using this Ruc-Wb123 construct, the immunoprecipitation assay was performed with a 96-well plate format at room temperature, essentially as described for other serologic tests (id.), except that an input of 10 million luminometer units (LU) of the enzyme reporter *Renilla* luciferase (Ruc) containing antigen(s) was used. Briefly, patient sera was diluted 1:10 in assay buffer (20 mM Tris, pH 7.5, 150 mM NaCl, 5 mM MgCl$_2$, 1% Triton X-100) in a 96-well polypropylene microtiter plate (Nunc, Roskilde, Denmark) and was added to 50 µl of 1×10$^7$ LU of Ruc-Wb123 in polypropylene plates. The plate was incubated for 5 minutes at room temperature after which the material was added to 7 µl of a 30% suspension of protein A/G beads in PBS (Pierce Biotechnology, Rockford, Ill.) in a 96-well filter HTS plate (catalog no. MSBVN1B50; Millipore, Bedford, Mass.). After 5 minutes, the filter plate containing the mixture was then applied to a vacuum manifold and washed twice in assay buffer and 8 times with PBS. After the final wash, all plates were processed on a Berthold LB 960 Centro microplate luminometer using a colenterazine substrate mix (Promega). All data were the average of triplicates that was corrected for background reactivity (no serum added).

All LU data presented were obtained from the averages for two independent experiments and corrected for background by subtracting LU values of beads incubated with L1SXP-1 Cos1 cell extract but no sera. A schematic of this assay protocol is provided in FIG. 1a.

For evaluating antibody titers by LIPS, 10 µl of diluted human sera (1 µl equivalent), 40 µl of assay buffer, and 50 µl of 1.0×10$^7$ light units (LU) of the Ruc-antigen Cos1 cell extract, diluted in assay buffer, were added to each well of a daughter polypropylene plate and allowed to incubate at room temperature on a rotary shaker for 1 hour. Next, 7 μl of a 30% suspension of protein A/G beads (Pierce) in PBS was added to the bottom of each well of a separate 96-well filter HTS plate (Millipore; catalogue number MSBVN1B50). The 100 μl antigen-antibody reaction mixture from each microtiter well was then transferred to the corresponding well of the filter plate and this plate was further incubated for 1 hour at room temperature on a rotary shaker. The filter plate containing the mixture was then applied to a vacuum manifold. The retained protein A/G beads were twice washed under suction with 0.2 ml of assay buffer, 8 times with 0.1 ml of assay buffer, and finally twice with 0.1 ml of PBS. After the final wash, the bottom of the plate was blotted and the LU measured in a Berthold Centro LB 960 plate reader luminometer using coelenterazine substrate mix (Promega). All LU data presented were obtained from the average of two independent experiments and corrected for background by subtracting LU values of beads incubated with Cos1 cell extract, but no sera.

For anti-IgG4 antibody determinations, the same protocol was utilized, with anti-IgG4 antibody beads substituted for protein A/G beads. The anti-IgG4 antibody beads were generated by combining 10 mg of an anti-IgG4 monoclonal antibody with Ultralink preactivated beads (Pierce Biotechnology, Boston, Mass.), as described by the manufacturer. The coupling efficiency was greater than 90%.

TABLE 1

Figure 3:
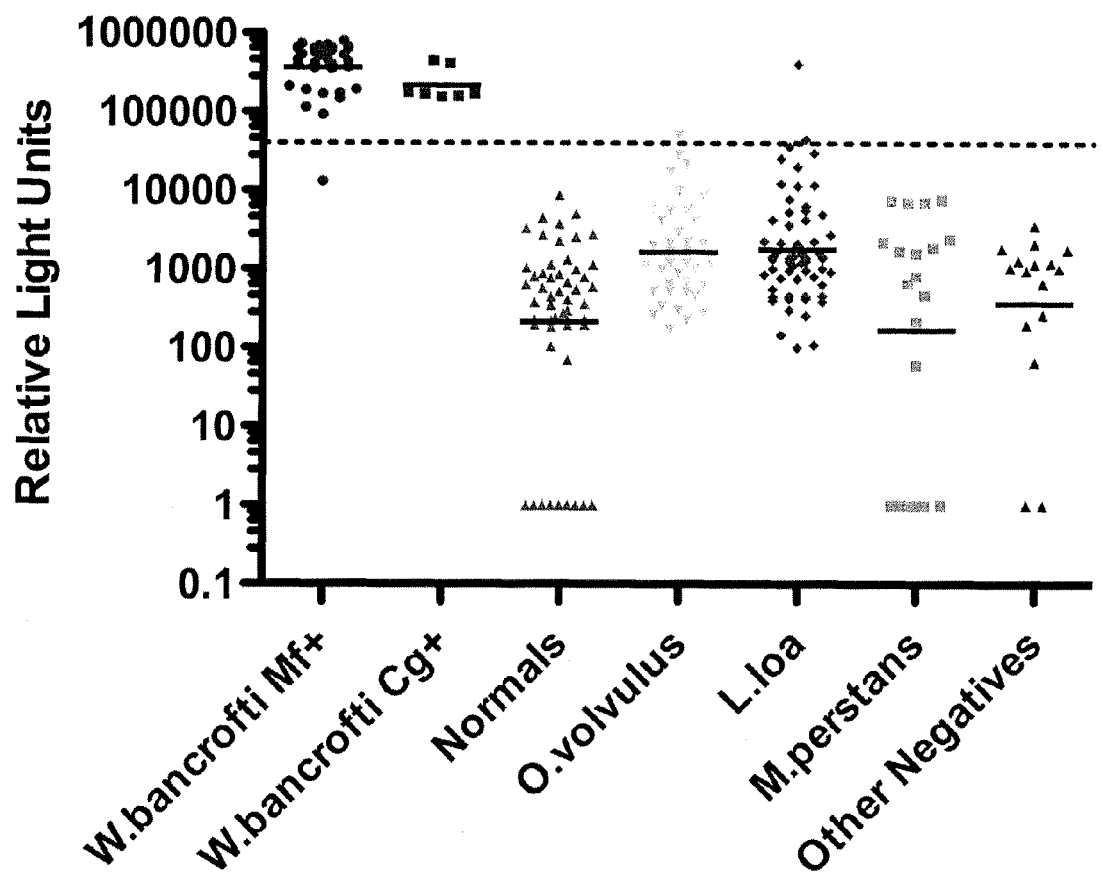
Figure 4:
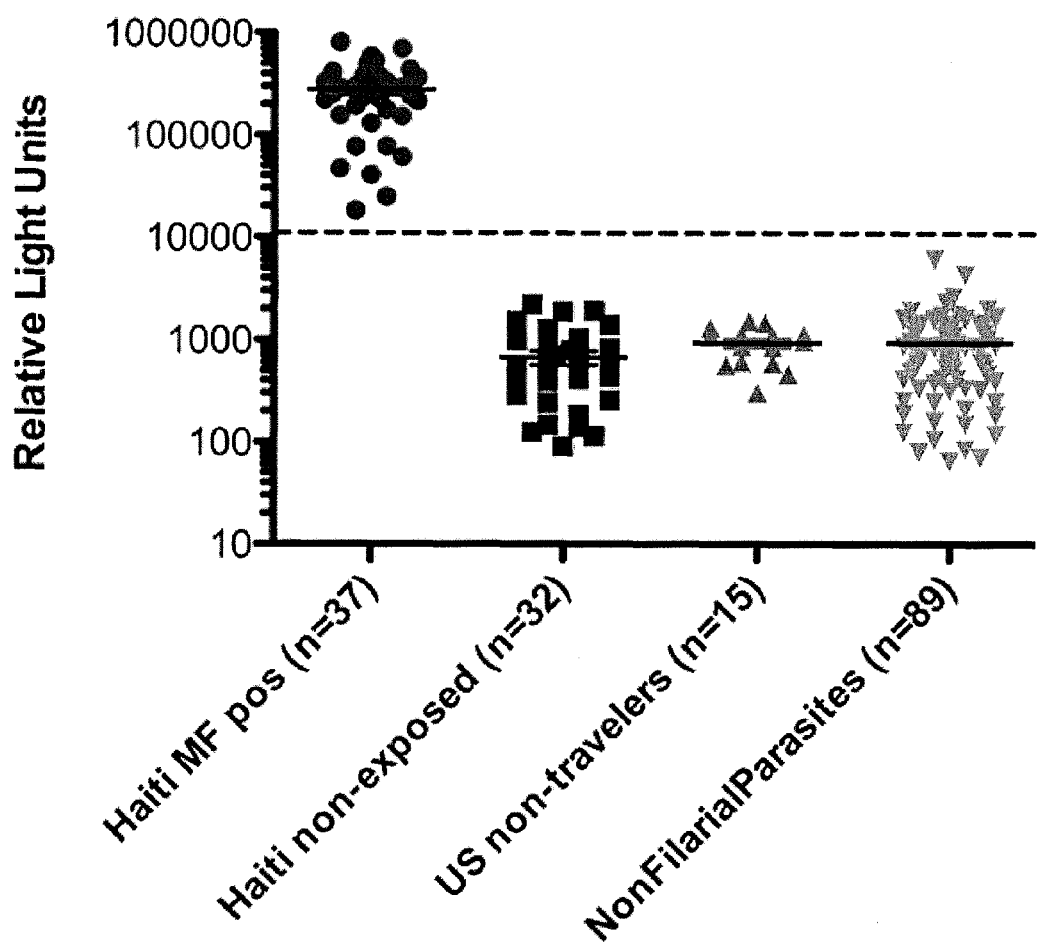

Performance of Wb123 based on composite date from FIG. 3.

| Compared to: | Normals | Other Parasites | Loa Loa | Onchocerciasis |
|---|---|---|---|---|
| Sensitivity | 100% | 100% | 98% | 98% |
| Specificity | 100% | 100% | 94% | 95% |
| PPV | 100% | 100% | 95% | 97% |
| NPV | 100% | 100% | 98% | 97% |

In the above table PPV and NPV mean positive predictive value and negative predictive value respectively. PPV is the likelihood that a positive value in a given test (in this case Wb123) predicts a true positive. NPV means is the likelihood that a negative test predicts a true negative. The closer to 100% the more likely the test is accurate.

Example 7

ELISA Assay. An ELISA based assay for total IgG using Wb123 antigen can be performed using the method of Lal, R. B., et al., *J. Infect. Dis.*, 158(5):1034-7 (1988). Briefly, Immulon 4 ELISA plates (Nunc) are coated with 100 μl of 1 μg/ml Wb123 antigen in coating buffer (sodium carbonate buffer, 0.045M NaHCO$_3$, 0.018M Na$_2$CO$_3$, pH 9.6) for about 2 hours or more at 37° C. and then overnight at 4° C. These plates may be stored at 4° C. (well sealed and wrapped) for up to six weeks.

The plates are then washed 6 times with wash buffer (PBS buffer pH 7.4, Tween 0.05%) and dry thoroughly. The plates were blocked with 200 μl/well of blocking buffer (PBS buffer pH 7.4, Tween 20 0.05%, BSA 1%) for 2 hours at 37° C.

The plates are again washed 6 times with wash buffer and dried thoroughly.

Individual sera were diluted in (PBS buffer pH 7.4, Tween 20 0.05%, BSA 1%), and added with standards and controls and incubated overnight. The plates are then washed 6 times with wash buffer and dried thoroughly. 100 μl/well of Alkaline phosphatase labelled goat anti-human IgG (Fc specific) 1:500 (Jackson Immunoresearch, West Grove, Pa.) are added to each well, and incubated at 37° C. for 2 hours.

The plates are again washed 6 times with wash buffer and dried thoroughly. 100 μl of Sigma 104 Phosphatase substrate (Sigma, St. Louis, Mo.) in Substrate Buffer (Na Carbonate pH 8.6) pH 8.6 (final concentration 1 μg/ml) is added to each well and allowed to react for about 10 minutes.

About 50 μl of 3 N NaOH is then added to each well to stop the reaction. The plates are then read in a microplate reader using Softmax software (Molecular Devices, Sunnyvale, Calif.).

Example 8

Serum levels of antigen-specific IgG antibodies to Wb123 can also be measured by ELISA. About 100 μl/well of Wb123 antigen at 10 μg/ml in coating buffer (as above) is added to the wells and incubated overnight at 4° C. The plates are then washed 6 times with wash buffer (PBS buffer pH 7.4, Tween 20 0.05%) and dry thoroughly. Block plates with 200 μl/well of blocking buffer (PBS buffer pH 7.4, Tween 20 0.05%, BSA 1%) for 2 hours at 37° C.

The plates are again washed 6 times with wash buffer and dried thoroughly.

Individual sera were diluted in (PBS buffer pH 7.4, Tween 20 0.05%, BSA 1%), and added with standards and controls and incubated overnight. The plates are again washed 6 times with wash buffer and dried thoroughly.

The appropriate mouse MAb (100 μl/well) IgG1 (6069) 1:1000 dilution IgG2 (6002) 1:5000 dilution IgG3 (6047) 1:5000 dilution IgG4 (6023) 1:5000 dilution, and incubated for about 2 hours at 37° C. The MAbs were produced at the Laboratory of Parasitic Diseases, NIAID, NIH from cell lines provided by Dr. Charles Reimer (CDC, Atlanta, Ga.). The Mabs can also be purchased from Hybridoma Reagent Labs (Baltimore, Md.).

The plates are again washed 6 times with wash buffer and dried thoroughly, followed by the addition of goat-antimouse IgG conjugated to alkaline phosphatase (100 μl/well; 1:500 dilution) for about 2 hours at 37° C.

The plates are again washed 6 times with wash buffer and dried thoroughly, and then developed with alkaline phosphatase substrate tablets (Sigma) dissolved in Na carbonate buffer (1 tablet/5 ml of buffer). The plates are then read in a microplate reader using Softmax software (Molecular Devices).

Example 9

Serum levels of antigen-specific IgE antibodies to Wb123 can also be measured by ELISA using sepharose/agarose containing anti-human IgE.

Resuspend beads in suppliers vial and remove 205 μl×the number of sera to be absorbed. Spin beads (which are in a 50% solution) at 3000 rpm for 10 minutes. Remove supernatant and resuspend beads to original volume in ELISA diluent (PBS buffer pH 7.4, Tween 20 0.05%, BSA 1%). This step is then repeated.

To 100 μl of serum, 200 μl of resuspended beads is added and the samples are incubated in a rocker overnight at 4° C. The samples are then microfuged at 14,000×g for about 10 minutes and the supernatant is transferred to a new tube. This supernatant will be approximately 200 μl and represents a 1:2 dilution of the original serum. This sample is then diluted further to 1:5 by adding 300 μl of ELISA diluent.

To ELISA plates coated with Wb123 antigen and blocked as in the above examples, the previously absorbed serum samples (100 µl/well; serial dilutions 1:5 and 1:50) are now added to the wells and incubated overnight at 4° C. The plates are washed as above and then anti-human IgE Mab 7.12 (1 mg/ml) (100 µl/well; 1:2500 dilution) is added and incubated for about 2 hours at 37° C. The plates are then read in a microplate reader using Softmax software (Molecular Devices).

The plates are washed and biotinylated goat-anti-mouse IgG (100 µl/well; 1:5000 dilution) (Jackson Immunoresearch) is added and incubated for about 2 hours at 37° C. This is followed by a wash and then strepavidin-alkaline phosphatase 1:1000 is added at room temperature and incubated for 1-2 hours. This is followed by a final wash and then the plates are developed with alkaline phosphatase substrate tablets (Sigma) dissolved in sodium carbonate buffer (1 tablet/5 ml of buffer).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for detecting presence of antibodies to *Wuchereria bancrofti* or *Brugia malayi* infective larvae (L3) in a sample, the method comprising:

a) contacting the sample with a first binding reagent which comprises a fusion protein having a reporter domain and a binding domain, the binding domain comprising Wb123 antigen, and forming an immunocomplex, wherein the Wb123 antigen is encoded by the polynucleotide sequence of SEQ ID NO: 1;

b) contacting the immunocomplex of a) with an immobilized second binding reagent, the second binding reagent being capable of binding to the antibodies if the antibodies are present in the sample, the first and second binding reagents being capable of simultaneously binding to the antibodies if the antibodies are present in the sample, such that the first binding reagent becomes immobilized through the antibodies bound to the second binding reagent;

c) detecting whether the first binding reagent has become immobilized to detect the presence or concentration of the antibodies; and d) correlating the detection of the immobilization of the first binding reagent with the presence of antibodies to *Wuchereria bancrofti* or *Brugia malayi* infective larvae (L3) in the sample.

2. The method of claim 1, wherein the reporter domain comprises *Renilla* luciferase.

3. The method of claim 1, wherein the first binding reagent comprises a Ruc-Wb123 antigen construct.

4. The method of claim 1, wherein the second binding reagent comprises protein A/G.

5. The method of claim 1, wherein c) further comprises adding a reporter domain substrate to the immunocomplex and second binding reagent of b).

6. The method of claim 5, wherein the reporter domain substrate comprises colenterazine.

7. The method of claim 1, wherein the sample is a human serum sample.

8. A method for detecting exposure to *Wuchereria bancrofti* or *Brugia malayi* in a subject, the method comprising:

a) obtaining a sample from a subject suspected of being exposed to *W. bancrofti* or *B. malayi*;

b) contacting the sample of a) with a mixture comprising a *Renilla* luciferase fusion protein comprising a Wb123 antigen to form an immunocomplex, wherein the Wb123 antigen is encoded by the polynucleotide sequence of SEQ ID NO: 1;

c) contacting the resulting immunocomplex of b) with a protein A/G binding substrate and binding the protein A/G binding substrate to the immunocomplex;

d) removing any unbound protein A/G binding substrate;

e) contacting the immunocomplex from d) with a luciferase substrate and incubating the mixture under conditions suitable to produce luminescence;

f) measuring the luminescence produced in the sample; and g) correlating the luminescence produced with exposure to *Wuchereria bancrofti* or *Brugia malayi*.

9. The method of claim 8, wherein the luciferase substrate comprises colenterazine.

10. A method for detecting a quantity of a specific antibody to Wb123 antigen in a sample, the method comprising:

(a) providing a Wb123 antigen which selectively forms a first immunocomplex with a sample antibody, the Wb123 antigen being directly bound to a solid support at a first location, wherein the Wb123 antigen is encoded by the polynucleotide sequence of SEQ ID NO: 1;

(b) providing an antibody which selectively forms a second immunocomplex with a sample antigen, the antibody being directly bound to the solid support at a second location;

(c) contacting the first location on the solid support with at least a portion of a biological sample under conditions whereby the first immunocomplex can form and contacting the second location on the solid support with at least a portion of the sample under conditions whereby the second immunocomplex can form;

(d) washing unbound material from the first location and from the second location;

(e) separately detecting whether the first immunocomplex is formed and whether the second immune complex is formed, the first immunocomplex being detected with a labeled antigen which selectively binds to the first immunocomplex, and the second immunocomplex being detected by adding a labeled antibody which selectively binds to the second complex, the labeled antibody being presented to both the first and the second locations; and (f) correlating the detection of the amount of labeled antibody being presented to both the first and the second locations with the amount of antibody in the sample.

\* \* \* \* \*